(12) United States Patent  
Cohn

(10) Patent No.: US 6,497,697 B1  
(45) Date of Patent: Dec. 24, 2002

(54) SYRINGE GUIDE AND VIAL HOLDER

(76) Inventor: Michael Cohn, 967 Rosewood Dr., San Mateo, CA (US) 94401

( * ) Notice: Subject to any disclaimer, the term of this patent is extended or adjusted under 35 U.S.C. 154(b) by 74 days.

(21) Appl. No.: 09/657,045

(22) Filed: Sep. 2, 2000

(51) Int. Cl.[7] .............................. A61B 19/00; B65B 3/04
(52) U.S. Cl. ..................... 604/414; 604/415; 141/27; 141/329; 141/330
(58) Field of Search .................... 604/414, 415, 604/411, 412, 413; 141/27, 329, 330

(56) References Cited

U.S. PATENT DOCUMENTS

| | | | |
|---|---|---|---|
| 2,677,372 A | * 5/1954 | Barnish, Jr. ............... | 604/414 |
| 3,602,272 A | 8/1971 | Stawski ..................... | 141/27 |
| 3,610,241 A | * 10/1971 | LeMarie | |
| 3,833,030 A | * 9/1974 | Waldbauer et al. | |
| 4,489,766 A | 12/1984 | Montada ..................... | 141/27 |
| D280,018 S | 8/1985 | Scott ........................ | D24/25 |
| 4,623,344 A | * 11/1986 | Eriksson .................... | 141/27 |
| 4,778,454 A | 10/1988 | LaDow ....................... | 604/208 |
| 5,240,047 A | * 8/1993 | Hedges ...................... | 141/27 |
| 5,247,972 A | 9/1993 | Tetreault ................... | 141/27 |
| 5,385,559 A | * 1/1995 | Mannix ...................... | 141/27 |
| 5,894,870 A | 4/1999 | Maxwell ..................... | 141/27 |
| 6,006,798 A | 12/1999 | Lindquist ................... | 141/27 |
| 6,162,199 A | * 12/2000 | Geringer .................... | 141/27 |
| 6,364,866 B1 | * 4/2002 | Furr et al. ................. | 141/330 |

* cited by examiner

*Primary Examiner*—Steven O. Douglas  
*Assistant Examiner*—Khoa Huynh

(57) ABSTRACT

A syringe guide and vial holder facilitates the insertion of a syringe into a medicine vial and the subsequent withdrawal of medicine from the vial into the syringe. The syringe guide and vial holder is constructed of a single piece of material and includes a vial holder for holding a medicine vial, a throat allowing access to the vial cap, and a syringe cradle for supporting a syringe.

2 Claims, 5 Drawing Sheets

SYRINGE GUIDE AND VIAL HOLDER

CROSS-REFERENCE TO RELATED APPLICATIONS

Not applicable.

BACKGROUND—Field of Invention

This invention relates to syringe guide and vial holders, specifically to such syringe guide and vial holders that are intended for use with a hypodermic syringe and a medicine-containing vial.

BACKGROUND—Description of Prior Art

This invention relates generally to devices for aiding in the self-use of syringes, and more particularly, to a guide for inserting a syringe needle into a medicine vial. When using a syringe to inject medicine, it is desirable to provide a guide or other device to facilitate filling the syringe with the desired medicine from the medicine vial. The guide helps align the syringe needle with the cap of the vial and provides a more stable connection between the syringe and the vial. While the use of syringe guide and vial holders has facilitated the use of syringes, especially by non-medically-trained people, the prior art syringe guide and vial holders have left many areas available for improvement. For example, many prior art syringe guide and vial holders fail to simplify the construction and use of syringe guide and vial holders (U.S. Pat. No. 5,247,972 to Tetreault (1993), U.S. Pat. No. 3,602,272 to Stawski (1971), and U.S. Pat. No. 4,489,766 to Montada (1984)). Some prior art syringe guide and vial holders require a vial to be seated in a trough or cylinder that precludes easy sterilization of the entire vial cover without removing the vial from the devices (U.S. Pat. No. 5,247,972 to Tetreault (1993), U.S. Pat. No. 5,894,870 to Maxwell (1999), U.S. Pat. No. 6,006,798 to Lindquist (1999), U.S. Pat. No. Des. 280,018 to Scott (1985), U.S. Pat. No. 4,489,766 to Montada (1984), and U.S. Pat. No. 4,778,454 to LaDow (1988)). Some prior art syringe guide and vial holders require a user to manipulate retaining bands to secure and release a vial and a syringe (U.S. Pat. No. 6,006,798 to Lindquist (1999)). This prior art overcomplicates the use of syringe guide and vial holders for many syringe users who only need a simple device to help steady the vial and the needle during the insertion process. In addition, the construction of some prior art syringe guide and vial holders has failed to allow precise positioning of a tip of a syringe needle into the reservoir of medicine in a vial (U.S. Pat. No. 3,602,272 to Stawski (1971) and U.S. Pat. No. 4,489,766 to Montada (1984)). To aid in fully extracting the last contents in the vial, the needle should be inserted into the vial no further than the neck of the vial so that when the vial is inverted, as is typically done when filling a syringe, the needle will be immersed in the medicine regardless of the amount of medicine remaining in the vial. The ability to precisely control the penetration depth is especially advantageous given today's high cost of medicine and the consequent desire to avoid waste. While the depth of the needle can always be statically set (U.S. Pat. No. 5,247,972 to Tetreault (1993), U.S. Pat. No. Des. 280,018 to Scott (1985), U.S. Pat. No. 4,489,766 to Montada (1984), and U.S. Pat. No. 4,778,454 to LaDow (1988)), a syringe guide and vial holder that allows manual adjustment of the penetration depth is especially helpful. Some prior art syringe guide and vial holders are specifically designed to accept only currently mass-produced syringes (U.S. Pat. No. 5,894,870 to Maxwell (1999), U.S. Pat. No. 6,006,798 to Lindquist (1999), U.S. Pat. No. Des. 280,018 to Scott (1985), U.S. Pat. No. 4,489,766 to Montada (1984), and U.S. Pat. No. 4,778,454 to LaDow (1988)). Any future variation to the specifications of the mass-produced syringes could render the syringe guide and vial holders unusable. The attributes of the present invention avoid this type of obsolescence. Another area for improvement of syringe guide and vial holders relates to their ease of cleaning (U.S. Pat. No. 5,247,972 to Tetreault (1993) and U.S. Pat. No. Des. 280,018 to Scott (1985)). The repeated use of a syringe guide and vial holder for administering medicine can result in spills of the medicine on the syringe guide and vial holder. The spills are desirably washed off. Some prior art syringe guide and vial holders, however, are constructed with difficult-to-clean crevices and pockets in the syringe guide and vial holder (U.S. Pat. No. 5,894,870 to Maxwell (1999), U.S. Pat. No. 6,006,798 to Lindquist (1999), U.S. Pat. No. 4,489,766 to Montada (1984), and U.S. Pat. No. 4,778,454 to LaDow (1988)). This means that the syringe guide and vial holder must be carefully washed and that makes the use of the syringe guide and vial holder more burdensome than necessary. Prior art syringe guide and vial holders have the cap of the medicine vial obstructed from full digital access when in normal position of use (U.S. Pat. No. 5,247,972 to Tetreault (1993), U.S. Pat. No. 5,894,870 to Maxwell (1999), U.S. Pat. No. 6,006,798 to Lindquist (1999), U.S. Pat. No. Des. 280,018 to Scott (1985), U.S. Pat. No. 4,489,766 to Montada (1984), and U.S. Pat. No. 4,778,454 to LaDow (1988)). Yet common medical protocol is to wipe the cap thoroughly with a sterilizing material immediately before use. The attributes of the present invention allow full access to the vial cap for the purpose of sterilization. Prior art syringe guide and vial holders have also suffered from allowing the medicine vial to be easily dislodged or jarred out of alignment with respect to the guide. Poor retention of a medicine vial makes a syringe guide and vial holder difficult to use, and often necessitates a user having to separately hold the vial using both hands. When the vial must be separately held, the ease of inserting the syringe needle is diminished. The ease of use is increased by removing any closed apertures on the syringe guide and vial holder through which a syringe must be carefully threaded. Additional ease of use is provided by designing the syringe guide and vial holder such that a syringe is easily positioned upon it. A need can therefore be seen for a new syringe guide and vial holder that overcomes all of these disadvantages of the prior art and fully takes into account the foregoing design considerations.

SUMMARY

In accordance with the present invention a syringe guide and vial holder comprises a holdable body, a cradling syringe support, and a grasping vial support.

OBJECTS AND ADVANTAGES

Accordingly, beside the objects and advantages of the syringe guide and vial holder described in my above patent, several objects and advantages of the present invention are:

a) to provide a syringe guide and vial holder for use by a person with limited manual dexterity;

b) to provide a syringe guide and vial holder for use by a person inexperienced in extracting medicines with a syringe;

c) to provide a syringe guide and vial holder that can be held securely by a human hand;

d) to provide a syringe guide and vial holder that can be held comfortably by a human hand;

e) to provide a syringe guide and vial holder for the re-use of a medicine vial without removal of the vial from the syringe guide and vial holder;

f) to provide a syringe guide and vial holder for the extraction of the last vestiges of liquid from a vial;

g) to provide a syringe guide and vial holder capable of being stored in a transportable refrigerating device;

h) to provide a syringe guide and vial holder capable of being stored in a refrigerator;

i) to provide a syringe guide and vial holder with clear access to a cap of a vial, for the purpose of sterilization, without a need to remove the vial from the syringe guide and vial holder;

j) to provide a syringe guide and vial holder that can be placed on a generally flat, horizontal surface without fear of tipping or rolling;

k) To provide a syringe guide and vial holder that can be cleaned by hand or by a dish-washing machine.

Further objectives, features, and advantages of my syringe guide and vial holder will become apparent from a consideration of the drawings and the ensuing description of certain preferred embodiments.

DRAWING FIGURES

In the drawings, closely related figures have the same number but different alphabetic suffixes.

REFERENCE NUMERALS IN DRAWINGS

| 20 | Syringe guide and vial holder | 37R | Outer edges |
|---|---|---|---|
| 22 | Syringe | 37L | Outer edges |
| 24 | Vial | 38 | Base of vial holder |
| 26 | Base | 39 | Interior end of cradle |
| 27 | Longitudinal axis | 40 | Vial body |
| 28R | Cradle rail | 41 | Interior end of grasping walls |
| 28L | Cradle rail | 42 | Vial neck |
| 29 | First end | 44 | Vial cap |
| 30 | Vial holder | 46 | Diaphragm |
| 31 | Second end | 48 | Syringe needle |
| 32 | Throat | 50 | Finger flange |
| 33 | Top surface | 52 | Plunger |
| 34 | Cradle end | 54L | Grasping wall |
| 36 | Vial holder end | 54R | Grasping wall |
| 29I | Inner edges | | |
| 29O | Outer edges | | |
| 29CL | Contact lines | | |

DESCRIPTION—FIGS. 1, 3, 4, 5,6, 7 and 8

Figure 1:
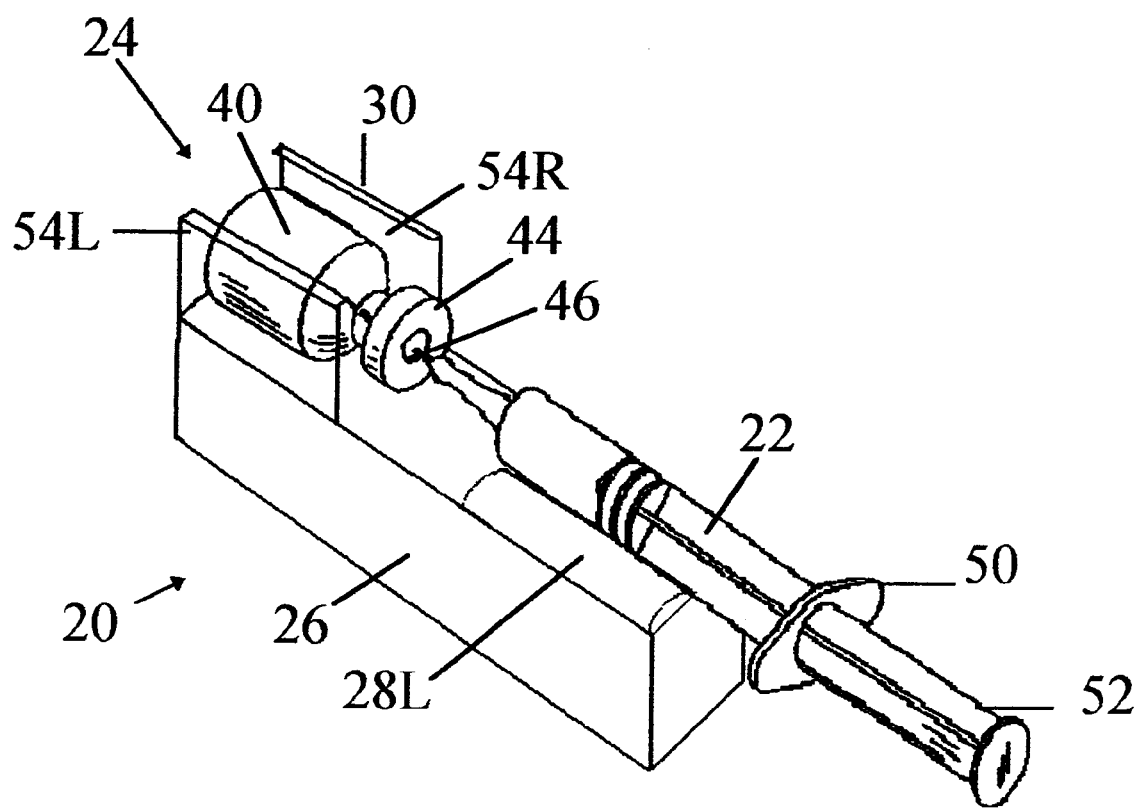
FIG. 1 shows a perspective view of a syringe guide and vial holder with a vial and a syringe in position of use.
Figure 3:
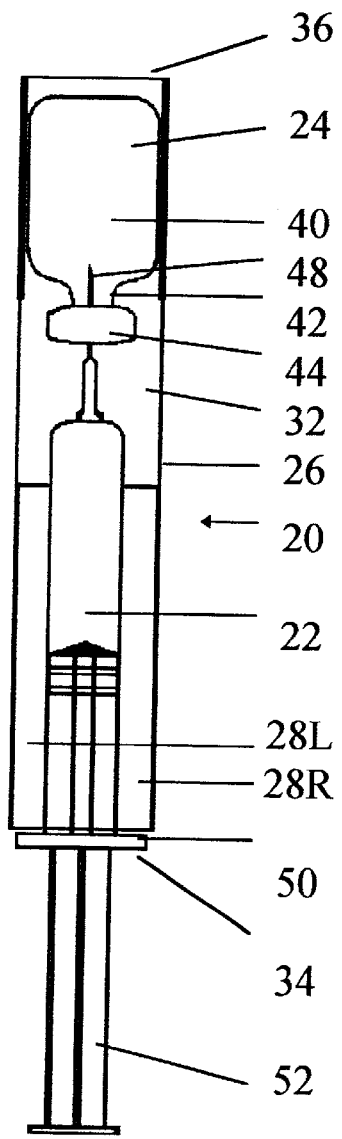
FIG. 3 shows a top view of a syringe guide and vial holder with a vial and a syringe in position of use.
Figure 4:
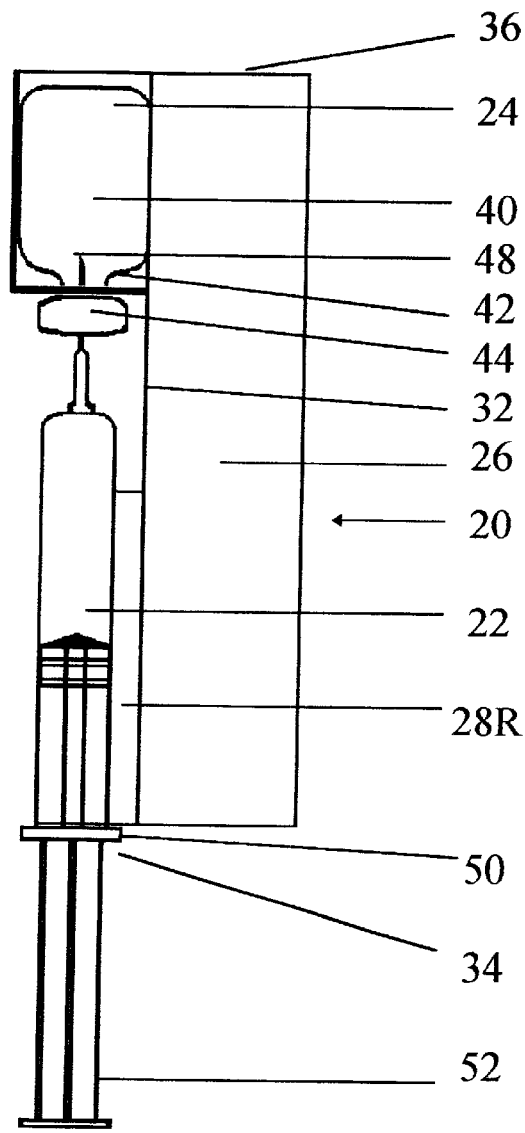
FIG. 4 shows a side view of a syringe guide and vial holder with a vial and a syringe in position of use.
Figure 5:
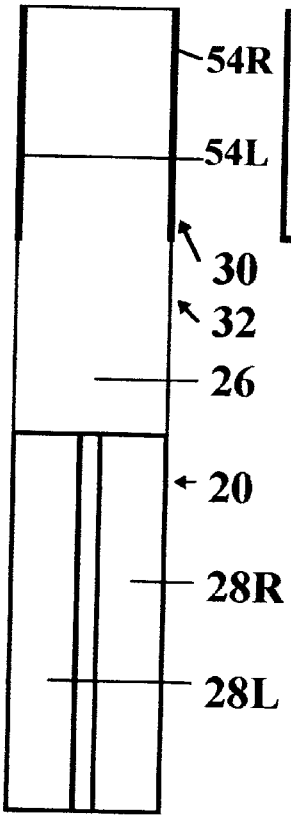
FIG. 5 shows a top view of a syringe guide and vial holder.
Figure 6:
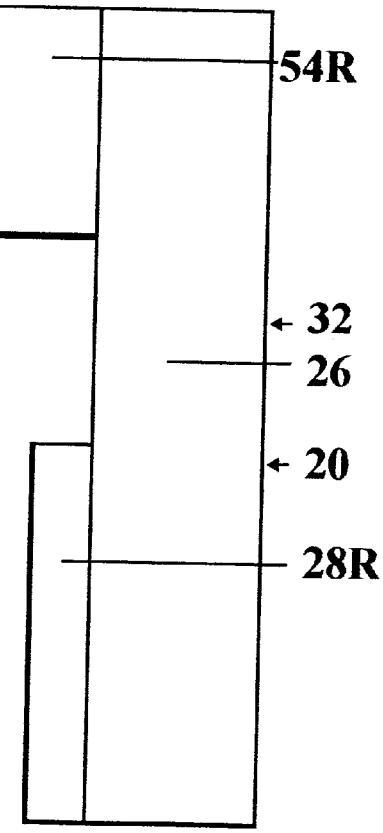
FIG. 6 shows a side view of a syringe guide and vial holder.

The present invention will now be described with reference to the accompanying drawings wherein like reference numerals correspond to like elements in the several drawings. The manner of using the syringe guide and vial holder 20 will usually be related to the use of a commercially-available syringe 22 and a pharmaceutical liquid-medicine vial 24 as shown in FIG. 1. FIG. 3 is a top view that shows the main parts of the syringe guide and vial holder in relation to each other with a syringe and vial in positions of use. FIG. 4 is a side view that shows the main parts of the syringe guide and vial holder in relation to each other with a syringe and vial in positions of use. FIG. 5 is a top view of an empty syringe guide and vial holder that shows the main parts in relation to each other. FIG. 6 is a side view of an empty syringe guide and vial holder that shows the main parts in relation to each other.

Figure 8:
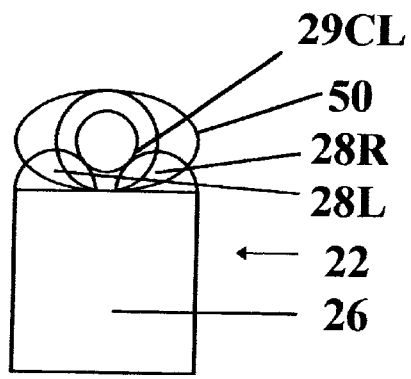
FIG. 8 shows an end view of a syringe guide and vial holder illustrating a syringe from the finger-flange end.

The support for a syringe is formed by a cradle rail 28L and a cradle rail 28R which are positioned in parallel with the elongated form of the syringe guide and vial holder base 26. FIG. 8 shows the cross-section of the cradle rail 28L and cradle rail 28R. This formation will accommodate almost any commercial syringe and position it into a centered, parallel alignment with the base 26. The syringe will also be supported at a predetermined height above the base 26. The predetermined height is engineered to be at the correct height for penetration of a syringe needle 48 into the diaphragm 46 of a medicine vial.

Figure 7:
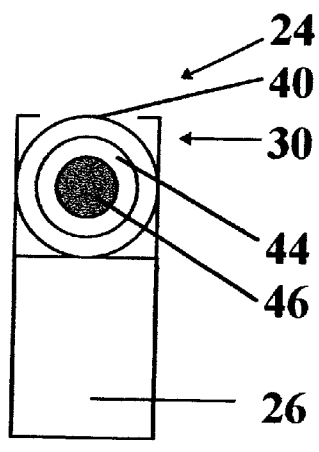
FIG. 7 shows a section view of a syringe guide and vial holder illustrating a vial from the cap end.

The support for the medicine vial is a vial holder 30 formed by the syringe guide and vial holder base 26, a left grasping wall 54L, and a right grasping wall 54R. Grasping wall 54L and grasping wall 54R are in parallel with cradle rail 28L and cradle rail 28R. Grasping wall 54L and grasping wall 54R are stiffly flexible. Grasping wall 54L and grasping wall 54R are tilted slightly towards each other at the top. The bases of grasping wall 54L and grasping wall 54R are slightly farther apart than the diameter of a standard medicine vial. This formation creates a holder for the medicine vial that grasps the vial slightly above its midline and forces the vial downward against the base of the vial holder 38. FIG. 7 shows a cap-end view of a vial in use position. The result is a stable grasping of the vial that has been forced into parallel with cradle rail 28L and cradle rail 28R. The paralleling of the various components of the syringe guide and vial holder 20 ultimately results in the desired positioning of a syringe needle 48 and the centerpoint of a vial cap 44. This paralleling alignment creates a nearly flawless method for introducing a syringe needle 48 in and through the diaphragm 46 of a vial 24 and ultimately into the reservoir of liquid in the vial body 40.

ADVANTAGES

From the description above, a number of advantages of my syringe guide and vial holder become evident:

(a) There will be a reduction in accidental puncture wounds commonly known as "sticks". This reduction is directly related to the distancing of the user's hand from the vial and the needle tip when using the syringe guide and vial holder.

(b) The simplicity of use of the syringe guide and vial holder will allow any normally coordinated person to fill a syringe from a vial without extensive training or practice.

(c) The ability to sterilize a vial cap without having to remove its vial allows for the entire syringe guide and vial holder, with the vial still in it, to be stored in a refrigerated area. Allowing the vial to be left in the invention reduces the amount of repeated handling of the vial and a subsequent reduction in vial mishandling.

(d) The use of moldable plastics will allow a commercial version of the syringe guide and vial holder to have a textured surface providing increased holdability.

(e) The use of moldable plastics will allow usage instructions to be permanently embossed into the syringe guide and vial holder for ease of reference.

OPERATION—FIGS. 1, 2, 3, 4 and 9

The operation of the present invention will now be described with reference to the accompanying drawings wherein like reference numerals correspond to like elements in the several drawings. The description will be of use by a right-handed person.

Figure 2:
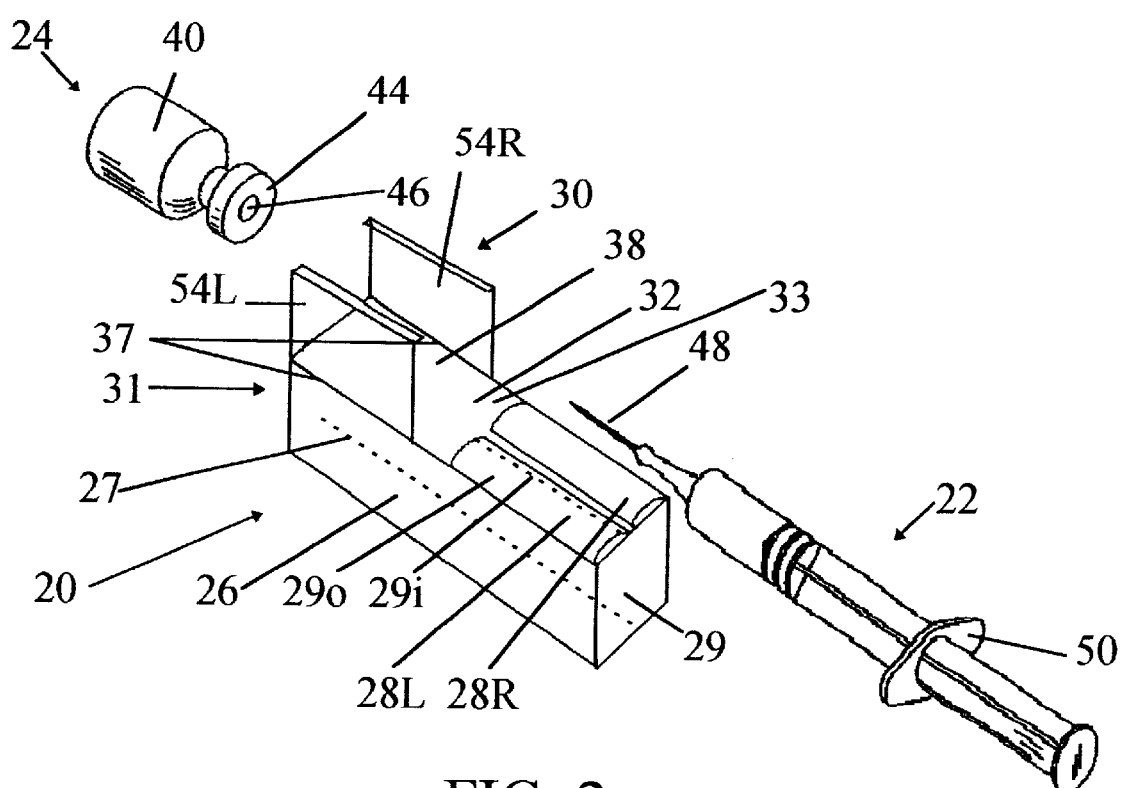
FIG. 2 shows a perspective view of a syringe guide and vial holder with a vial and a syringe retracted from use.
Figure 9:
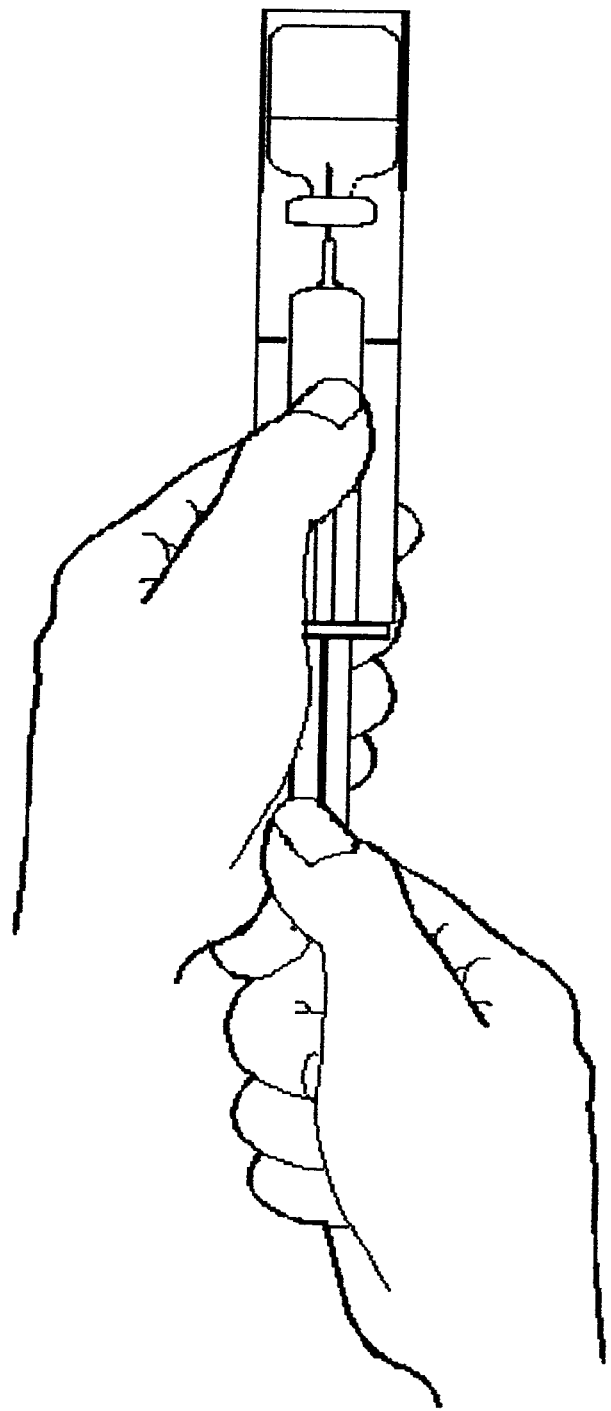
FIG. 9 shows a view of a syringe guide and vial holder being used by two hands.

The manner of using the syringe guide and vial holder 20 will usually be related to the use of a commercially-available syringe 22 and a pharmaceutical liquid-medicine vial 24 as shown in FIG. 1. FIG. 2 shows the general orientation of a syringe 22 and a vial 24 to the syringe guide and vial holder 20 prior to use. The vial 24 is readied for use according to the instructions of its manufacturer. The vial 24 is manipulated horizontally from the vial holder end 36 into the center of the vial holder 30 with the vial cap 44 pointing towards the throat 32 of the syringe guide and vial holder 20. When installed, the flat base of the vial 24 is generally flush with the vial holder end 36. The vial body 40 will be supported and contained by the base of vial holder 38, the left grasping wall 54L, and the right grasping wall 54R. The vial 24 is manually adjusted to be firmly within the grasp of the vial holder 30 with the vial cap 44 and vial neck 42 protruding over the throat 32 of the syringe holder 20. The adjusted position of the vial 24 allows the diaphragm 46 of the vial cap 44 to be fully accessed for sterilization. The syringe 22 is readied for use according to the instructions of its manufacturer. The syringe 22 will be placed on and between the cradle rail 28L and cradle rail 28R with the syringe needle 48 pointing toward the throat 32 of the base of the syringe guide and vial holder 26. The positioning of the syringe 22 on the cradle rail 28L and cradle rail 28R causes the syringe needle 48 to be aligned with the penetrable diaphragm 46 of the vial cap 44 as shown in FIG. 3 and FIG. 4. Moderate pressure by a user's left thumb holds the syringe 22 upon cradle rail 28R and cradle rail 28L as shown in FIG. 9. The syringe 22 will now be slid manually towards the secured vial so that the syringe needle 48 passes through the diaphragm 46 of the vial cap 44 and enters the liquid medicine in the vial 24 as shown in FIG. 1, FIG. 3, FIG. 4 and FIG. 9. At the cradle end 34 the finger-flange 50 and the plunger 52 will be in close proximity to the cradle rail 28L and cradle rail 28R as shown in FIG. 8. The plunger 52 will be grasped by the thumb and fingers of the right hand as shown in FIG. 9. Normal manipulation of the plunger 52 causes liquid medicine from the vial 24 to be drawn into the cavity of the syringe 22. The syringe 22 is now filled and can be removed from the cradle rail 28L and cradle rail 28R.

While the present invention has been described in terms of the preferred embodiments discussed in the above specification, it will be understood by one skilled in the art that the present invention is not limited to these particular preferred embodiments, but includes any and all such modifications that are within the spirit and scope of the present invention as defined in the appended claims.

CONCLUSION, RAMIFICATIONS, AND SCOPE

Accordingly, the reader will see that the syringe guide and vial holder can be used to facilitate the extraction of liquids from medicine vials into syringes. Furthermore, the syringe guide and vial holder has the following additional advantages in that:

it permits use by a person with limited manual dexterity;

it permits use by a person inexperienced in extracting medicines with a syringe;

it permits a syringe guide and vial holder to be securely held by a human hand;

it permits a syringe guide and vial holder to be held comfortably by a human hand;

it permits the re-use of a medicine vial without removal of the vial from the syringe guide and vial holder;

it permits the extraction of the last vestiges of liquid from a vial;

it permits storage of a vial and syringe guide and vial holder in a transportable refrigerating device;

it permits storage of a vial and syringe guide and vial holder in a stationary refrigerating device;

it permits sterilization of the vial cap without removal of the vial from the syringe guide and vial holder;

it permits a syringe guide and vial holder with a vial in use position to be placed on a generally flat, horizontal surface without fear of tipping or rolling;

It permits a syringe guide and vial holder to be cleaned by hand or by a dishwashing machine.

Although the description above contains many specifications, these should not be construed as limiting the scope of the syringe guide and vial holder but as merely providing illustrations of some of the presently preferred embodiments of the syringe guide and vial holder. Thus the scope of the syringe guide and vial holder should be determined by the appended claims and their legal equivalents, rather than by the examples given.

I claim:

1. A syringe guide and vial holder, comprising:

a one-piece construction body having a top surface and a longitudinal axis, said top surface having a first end and an opposite second end;

a cradle for supporting a barrel of a syringe, said cradle consists of a pair of separated, dome-shaped cradle rails, said pair of cradle rails forming on said first end and protruding upwardly from said top surface, said pair of cradle rails are parallel to the longitudinal axis of the body, each of said pair of cradle rails having inner and outer spaced edges, wherein said inner edges of said pair of cradle rails defining elongated contact lines supporting the barrel of the syringe to aid in sliding movement of the syringe;

a vial holder forming on said opposite second end, said vial holder consists of a pair of grasping walls that are in parallel with the longitudinal axis of the body, said pair of grasping walls forming on outer edges of said body and extending upwardly, said pair of grasping walls slightly tilting toward each other at the top to create a downward force for securing a vial; and a throat consisting of a space defined between an interior end of said cradle and an interior end of said vial holder, said throat adapted to be larger than a width of an adult human thumb;

wherein said syringe guide and vial holder will aid in the filling of the syringe from the vial.

2. The syringe guide and vial holder of claim 1, wherein said syringe guide and vial holder is constructed of a plastic material.

* * * * *